(12) United States Patent
Spesard et al.

(10) Patent No.: US 10,231,456 B2
(45) Date of Patent: Mar. 19, 2019

(54) METHODS AND COMPOSITIONS FOR CONTROLLING WEED INFESTATION AND IMPROVING GRASS QUALITY

(71) Applicant: BAYER CROPSCIENCE LP, Research Triangle Park, NC (US)

(72) Inventors: Bruce Spesard, Wake Forest, NC (US); Don Myers, Wake Forest, NC (US); Laurence Mudge, Central, SC (US); Matt Bradley, Cary, NC (US)

(73) Assignee: BAYER CROPSCIENCE LP, Research Triangle, NC (US)

( * ) Notice: Subject to any disclaimer, the term of this patent is extended or adjusted under 35 U.S.C. 154(b) by 0 days.

(21) Appl. No.: 15/694,263

(22) Filed: Sep. 1, 2017

(65) Prior Publication Data
US 2017/0367342 A1    Dec. 28, 2017

Related U.S. Application Data

(63) Continuation of application No. 13/902,364, filed on May 24, 2013, now Pat. No. 9,781,934.

(60) Provisional application No. 61/652,558, filed on May 29, 2012.

(51) Int. Cl.
*A01N 47/34*    (2006.01)
*A01N 47/36*    (2006.01)

(52) U.S. Cl.
CPC .............. *A01N 47/34* (2013.01); *A01N 47/36* (2013.01)

(58) Field of Classification Search
CPC .............................. A01N 47/36; A01N 47/34
See application file for complete search history.

(56) References Cited

U.S. PATENT DOCUMENTS

| | | | | |
|---|---|---|---|---|
| 7,465,857 | B1 * | 12/2008 | van 't Klooster | A01H 5/10 800/260 |
| 7,781,374 | B2 * | 8/2010 | Feucht | A01N 47/38 504/139 |
| 2009/0203526 | A1 | 8/2009 | Haikal et al. | |
| 2010/0261680 | A1 | 10/2010 | Feucht et al. | |
| 2010/0292082 | A1 | 11/2010 | Walter et al. | |
| 2011/0269626 | A1 | 11/2011 | James et al. | |

OTHER PUBLICATIONS

International Search Report and Written Opinion of PCT/US2013/042608 dated Jan. 22, 2014.

* cited by examiner

*Primary Examiner* — Johann R Richter
*Assistant Examiner* — Danielle Sullivan
(74) *Attorney, Agent, or Firm* — McBee Moore Woodward & Vanik IP, LLC; Susan McBee

(57) ABSTRACT

Methods for controlling unwanted vegetation, such as weeds, to turfgrass by applying an active compound combination including a triazolinone herbicide, for example, sulfonylamino-carbonyl-triazolinone, and at least one sulfonylurea herbicides, to turfgrass is described herein. The disclosure also provides for active compound combinations and methods of improving turfgrass quality.

16 Claims, No Drawings

METHODS AND COMPOSITIONS FOR CONTROLLING WEED INFESTATION AND IMPROVING GRASS QUALITY

This application is a continuation of U.S. application Ser. No. 13/902,364, filed May 24, 2013, which claims priority to U.S. Provisional Application No. 61/652,558, filed May 29, 2012, the contents of each are incorporated herein by reference in their entireties.

FIELD

Methods for controlling unwanted vegetation, such as weeds, to turfgrass by applying an active compound combination including a triazolinone herbicide, for example, sulfonylamino-carbonyl-triazolinone, and at least one sulfonylurea herbicide, to turfgrass is described herein. The disclosure also provides for active compound combinations and methods of improving turfgrass quality.

BACKGROUND

Grass lawns and turfgrass are dominant landscape features of many residences and commercial properties. Turfgrass are also increasingly prevalent in gardens and recreational areas, such as golf courses. Given the high visibility of these recreational, residential, and commercial areas, maintaining the color, uniformity, and durability of grass is of continued importance.

A wide variety of grass, such as turfgrass, is susceptible to unwanted vegetation, such as annual and perennial grass weeds, sedges and kyllingas, and broadleaf weeds, that negatively influences both the quality and durability of the grass. Such weeds include dallisgrass (*Paspalum dilatatum*), sedges (*Cyperus* spp.), kyllingas (*Kyllinga* spp.), bull *paspalum* (*Paspalum setaceum*), vaseygrass (*Paspalum urvillei*), Alexandergrass (*Brachiaria plantaginea*), tropical signalgrass (*Urochloa subquadripara*), goosegrass (*Eleusine indica*), doveweed (*Murdannia nudiflora*), creeping bentgrass (*Agrostis stolonifera*), annual bluegrass (*Poa annua*), roughstalk bluegrass (*Poa trivia/is*), transition ryegrass (*lolium* spp.), tall fescue (*Schedonorus phoenix IFestuca arundinacea*), and crabgrass (*Digitaria* spp.), dollarweed/pennywort (*Hydrocotyle* spp.), spurge (*Chamaescyce* spp.), Virginia buttonweed (*Diodia virginiana*), little barley (*Hordeum pusillum*), carpetweed (*Mollugo verticillata*), common chickweed (*Ste/Zaria media*), mouseear chickweed (*Cerastium vulgatum*), hop clover (*Trifolium* spp.), rabbitfoot clover (*Trifolium arvense*), white clover (*trifolium repens*), common vetch (*Vicia sativa*), cudweed (*Gnaphalium, Pseusdognaphalium* and *Gamochaeta* spp.), cutleaf evening primrose (*Oenothera laciniata*), Carolina false dandelion (*Pyrrhopappus carolinianus*), Florida pusley (*Richardia scabra*), hairy bittercress (*Cardamine hirsuta*), henbit (*Lamium amplexicaule*), knawel (*Scleranthus annuus*), London rocket (*Sisymbrium irio*), buckhorn plantain (*Plantago lanceolata*), paleseed plantain (*Plantago virginica*), sphepherdspurse (*Capsella bursa-pastoris*), corn speedwell (*Veronica arvensis*), Texas toadflax (*Nuttallanthus texanus*), common cocklebur (*Xanthium strumarium*), Philadelphia fleabane (*Erigeron philadelphicus*), Venice mallow (*Hibiscus trionum*), maypop passionflower (*Passiflora incarnata*), redroot pigweed (*Amaranthus retroflexus*), common pokeweed (*Phytolacca Americana*), wild radish (*Raphanus raphanistrum*), common ragweed (*Ambrosia artemisiifolia*), giant ragweed (*Ambrosia trifida*), Pennsylvania smartweed (*Polygonum pensylvanicum*), common sunflower (*Helianthus annus*), velvetleaf (*Abutilon theophrasti*), bahiagrass (*Paspalum notatum*), Carolina geranium (*Geranium carolinanum*), parsley-piert (*Aphanes microcarpa*), spurge (*Chamaesyce* spp.), and yellow woodsorrel (*Oxalis stricta*).

The weeds detract from the beauty of lawns due to the contrast in color and texture between the desired grass plants and the weeds. Consequently, weeds detract from the uniformity of a turf and add to its maintenance requirements. In addition, the weeds compete with the desired grass plants for available water and nutrients, usually resulting in thinning of desirable plant cover.

Active compound combinations comprising known substituted thien-3-yl-sulphonylamino(thio)carbonyltriazolin (ethi)one and one or more known herbicidally active compounds are known to be effective herbicides (US 2010/0261680, US 2009/0203526).

SUMMARY

In an aspect, the disclosure provides for an active compound combination comprising a triazolinone herbicide, for example sulfonylamino-carbonyl-triazolinone, and at least one sulfonylurea herbicide.

Examples of triazolinone herbicide include sulfentrazone and thiencarbazone-methyl, and examples of a sulfonylurea herbicide include foramsulfuron, flazasulfuron, and rimsulfuron, halosulfuron-methyl, sulfosulfuron, and trifloxysulfuron-sodium.

In an aspect, the disclosure provides for an active compound combination comprising thiencarbazone-methyl and halosulfuron-methyl. In an aspect, the disclosure provides for an active compound combination comprising thiencarbazone-methyl and furamsulfuron.

In an aspect, the disclosure provides for an active compound combination comprising a triazolinone herbicide, for example sulfonylamino-carbonyl-triazolinone, and two sulfonylurea herbicides.

Examples of triazolinone herbicide include sulfentrazone and thiencarbazone-methyl, and examples of one sulfonylurea herbicide include foramsulfuron, flazasulfuron, and rimsulfuron, and examples of the other sulfonylurea herbicide include halosulfuron-methyl, sulfosulfuron, and trifloxysulfuron-sodium.

In an aspect, the disclosure provides for an active compound combination comprising thiencarbazone-methyl, foramsulfuron, and halosulfuron-methyl.

In an aspect, the disclosure provides for a method of controlling weeds in turfgrass by applying the active compound combination described herein to turfgrass.

In an aspect, the weeds are monocotyledonous weeds. In an aspect, the weeds are dicotyledonous weeds.

In an aspect, an active compound combination described herein are applied to turfgrass in separate application steps or together in the same application step.

In an aspect, the disclosure provides for a combination described herein at a ratio of about 0.5 to 50:0.5-15 for triazolinone herbicide to a sulfonylurea herbicide. In an aspect, the disclosure provides for a combination described herein at a ratio of about 0.5 to 25:0.5-10 for triazolinone herbicide to a sulfonylurea herbicide.

In an aspect, the disclosure provides for a combination described herein with about 5% to about 15% by weight of a triazolinone herbicide, and about 15% to about 25% of a sulfonylurea herbicide, and about 25% to about 35% by weight of another sulfonylurea herbicide.

In an aspect, the disclosure provides for a combination described herein at a ratio of about 0.1 to 10:0.1 to 10:0.1 to 20 for triazolinone herbicide to sulfonylurea herbicide to sulfonylurea herbicide. In an aspect, the disclosure provides for a combination described herein at a ratio of about 0.1 to 5:0.1 to 5:0.1 to 10 for triazolinone herbicide to sulfonylurea herbicide to sulfonylurea herbicide. In an aspect, the disclosure provides for a combination described herein at a ratio of about 0.5 to 1.5:1.5 to 2.5:2.5 to 3.5 for triazolinone herbicide to sulfonylurea herbicide to sulfonylurea herbicide.

The disclosure also provides for a combination described herein with about 5% to 15% by weight of thiencarbazone-methyl, about 15% to 25% by weight of foramsulfuron, and about 25% to 35% by weight of halosulfuron-methyl.

In an aspect, the disclosure also provides for a combination described herein with about 9.9% by weight of thiencarbazone-methyl, about 19.8% by weight of foramsulfuron, and about 30.8% by weight of halosulfuron-methyl.

In an aspect, the disclosure provides for a combination described herein at a ratio of about 0.1 to 10:0.1 to 10:0.1 to 20 for for thiencarbazone-methyl to foramsulfuron to halosulfuron-methyl. In an aspect, the disclosure provides for a combination described herein at a ratio of about 0.1 to 5:0.1 to 5:0.1 to 10 for thiencarbazone-methyl to foramsulfuron to halosulfuron-methyl. In an aspect, the disclosure provides for a combination described herein at a ratio of about 0.5 to 1.5:1.5 to 2.5:2.5 to 3.5 for thiencarbazone-methyl to foramsulfuron to halosulfuron-methyl.

In an aspect, the disclosure also provides for a combination described herein at a ratio of about 1:2:3 for thiencarbazone-methyl to foramsulfuron to halosulfuron-methyl.

In an aspect, a combination described herein is applied to turfgrass at an application rate of about 0.605 to 1.936 oz active ingredient/A. In an aspect, a combination described herein is applied to turfgrass at a rate of about 0.605 oz active ingredient/A. In an aspect, a combination described herein is applied to turfgrass at a rate of about 1.21 oz active ingredient/A. In an aspect, a combination described herein is applied to turfgrass at a rate of about 1.815 oz active ingredient/A. In an aspect, a combination described herein is applied to turfgrass at a rate of about 1.936 oz active ingredient/A.

In an aspect, a combination described herein is applied to turfgrass at a seasonal maximum rate of about 3.872 oz active ingredient/A.

DETAILED DESCRIPTION

The disclosure also provides for a method of treating turfgrass with a combination described herein.

In an aspect, the disclosure provides for a method of treating weed infestation of turfgrass. In another aspect, the weed is monocotyledonous weed. In another aspect, the weed is dicotyledonous weed.

The disclosure also provides for a method of improving the quality of turfgrass by applying a combination described herein to grass to treat weed infestation.

In an aspect, the disclosure provides for an active compound combination comprising a triazolinone herbicide, for example, sulfonylamino-carbonyltriazolinone, and at least one sulfonylurea herbicide.

Examples of triazolinone herbicide include sulfentrazone and thiencarbazone-methyl, and examples of sulfonylurea herbicide include foramsulfuron, flazasulfuron, and rimsulfuron, halosulfuron-methyl, sulfosulfuron, and trifloxysulfuron-sodium.

In an aspect, the disclosure provides for an active compound combination comprising thiencarbazone-methyl and halosulfuron-methyl. In an aspect, the disclosure provides for an active compound combination comprising thiencarbazone-methyl and foramsulfuron.

In an aspect, the disclosure provides for an active compound combination comprising a triazolinone herbicide, for example, sulfonylamino-carbonyltriazolinone, and two sulfonylurea herbicides.

Examples of triazolinone herbicide include sulfentrazone and thiencarbazone-methyl, and examples of one sulfonylurea herbicide include foramsulfuron, flazasulfuron, and rimsulfuron, and examples of the other sulfonylurea herbicide include halosulfuron-methyl, sulfosulfuron, and trifloxysulfuron-sodium.

In an aspect, the disclosure provides for an active compound combination comprising thiencarbazone-methyl, foramsulfuron, and halosulfuron-methyl.

Surprisingly, it has now been found that the above-defined active compound combination comprising a triazolinone herbicide and at least one sulfonylurea herbicide, for example thiencarbazone-methyl, foramsulfuron, and halosulfuron-methyl, exhibit a particularly high herbicidal activity combined with turfgrass compatability, and can be used for the selective control of weeds in turfgrass.

Surprisingly, the herbicidal activity of the active compound combination according to the invention exceeds the total of the action of the individual active compounds considerably.

Thus, not just a complementation of actions but a synergistic effect is present which could not have been predicted. The active compound combinations are well tolerated in a variety of warm season turfgrasses also effecting good control of weeds which are usually difficult to control. Thus, the novel active compound combinations are a valuable addition to the herbicides.

The synergistic effect of the active compound combinations according to the invention is particularly strongly pronounced in certain concentration ratios. However, the weight ratios of the active compounds in the active compound combinations may be varied within relatively wide ranges.

In an aspect, the disclosure provides for a combination described herein at a ratio of about 0.5 to 50:0.5-15 for triazolinone herbicide to a sulfonylurea herbicide. In an aspect, the disclosure provides for a combination described herein at a ratio of about 0.5 to 25:0.5-10 for triazolinone herbicide to a sulfonylurea herbicide.

In an aspect, the disclosure provides for a combination described herein at a ratio of about 1:3 for triazolinone herbicide to a sulfonylurea herbicide. In an aspect, the disclosure provides for a combination described herein at a ratio of about 5:1 for triazolinone herbicide to a sulfonylurea herbicide. In an aspect, the disclosure provides for a combination described herein at a ratio of about 7.6:1 for triazolinone herbicide to a sulfonylurea herbicide. In an aspect, the disclosure provides for a combination described herein at a ratio of about 15.1:1 for triazolinone herbicide to a sulfonylurea herbicide. In an aspect, the disclosure provides for a combination described herein at a ratio of about 22.7:1 for triazolinone herbicide to a sulfonylurea herbicide.

In an aspect, In an aspect, the disclosure provides for a combination described herein with about 5% to 15% by weight of a triazolinone herbicide, about 15% to 25% by weight of a first sulfonylurea herbicide, and about 25% to 35% by weight of a second sulfonylurea herbicide.

The disclosure also provides for a combination described herein with about 5% to 15% by weight of thiencarbazone-methyl, about 15% to 25% by weight of foramsulfuron, and about 25% to 35% by weight of halosulfuron-methyl.

In an aspect, the disclosure also provides for a combination described herein with about 9.9% by weight of thiencarbazone-methyl, about 19.8% by weight of foramsulfuron, and about 30.8% by weight of halosulfuron-methyl.

In an aspect, the disclosure provides for a combination described herein at a ratio of about 0.1 to 10:0.1 to 10:0.1 to 20 for triazolinone herbicide to a first sulfonylurea herbicide to a second sulfonylurea herbicide. In an aspect, the disclosure provides for a combination described herein at a ratio of about 0.1 to 5:0.1 to 5:0.1 to 10 for triazolinone herbicide to a first sulfonylurea herbicide to a second sulfonylurea herbicide. In an aspect, the disclosure provides for a combination described herein at a ratio of about 0.5 to 1.5:1.5 to 2.5:2.5 to 3.5 for triazolinone herbicide to a first sulfonylurea herbicide to a second sulfonylurea herbicide.

In an aspect, the disclosure provides for a combination described herein at a ratio of about 1:1.5:2.4 for triazolinone herbicide to a first sulfonylurea herbicide to a second sulfonylurea herbicide. In an aspect, the disclosure provides for a combination described herein at a ratio of about 1:2:1 for triazolinone herbicide to a first sulfonylurea herbicide to a second sulfonylurea herbicide. In an aspect, the disclosure provides for a combination described herein at a ratio of about 1:2:2 for triazolinone herbicide to a first sulfonylurea herbicide to a second sulfonylurea herbicide. In an aspect, the disclosure provides for a combination described herein at a ratio of about 1:2:3 for triazolinone herbicide to a first sulfonylurea herbicide to a second sulfonylurea herbicide. In an aspect, the disclosure provides for a combination described herein at a ratio of about 1:2:6 for triazolinone herbicide to a first sulfonylurea herbicide to a second sulfonylurea herbicide. In an aspect, the disclosure provides for a combination described herein at a ratio of about 1:2:6.2 for triazolinone herbicide to a first sulfonylurea herbicide to a second sulfonylurea herbicide. In an aspect, the disclosure provides for a combination described herein at a ratio of about 1.5:1:4.8 for triazolinone herbicide to a first sulfonylurea herbicide to a second sulfonylurea herbicide. In an aspect, the disclosure provides for a combination described herein at a ratio of about 2:1:3.1 for triazolinone herbicide to a first sulfonylurea herbicide to a second sulfonylurea herbicide. In an aspect, the disclosure provides for a combination described herein at a ratio of about 3:2:1 for triazolinone herbicide to a first sulfonylurea herbicide to a second sulfonylurea herbicide.

In an aspect, the disclosure provides for a combination described herein at a ratio of about 0.1 to 10:0.1 to 10:0.1 to 20 for for thiencarbazone-methyl to foramsulfuron to halosulfuron-methyl. In an aspect, the disclosure provides for a combination described herein at a ratio of about 0.1 to 5:0.1 to 5:0.1 to 10 for thiencarbazone-methyl to foramsulfuron to halosulfuron-methyl. In an aspect, the disclosure provides for a combination described herein at a ratio of about 0.5 to 1.5:1.5 to 2.5:2.5 to 3.5 for thiencarbazone-methyl to foramsulfuron to halosulfuron-methyl.

In an aspect, the disclosure provides for a combination described herein at a ratio of about 1:1.5:2.4 for thiencarbazone-methyl to foramsulfuron to halosulfuron-methyl. In an aspect, the disclosure provides for a combination described herein at a ratio of about 1:2:1 for thiencarbazone-methyl to foramsulfuron to halosulfuron-methyl. In an aspect, the disclosure provides for a combination described herein at a ratio of about 1:2:2 for thiencarbazone-methyl to foramsulfuron to halosulfuron-methyl. In an aspect, the disclosure provides for a combination described herein at a ratio of about 1:2:3 for thiencarbazone-methyl to foramsulfuron to halosulfuron-methyl. In an aspect, the disclosure provides for a combination described herein at a ratio of about 1:2:6 for thiencarbazone-methyl to foramsulfuron to halosulfuron-methyl. In an aspect, the disclosure provides for a combination described herein at a ratio of about 1:2:6.2 for thiencarbazone-methyl to foramsulfuron to halosulfuron-methyl. In an aspect, the disclosure provides for a combination described herein at a ratio of about 1.5:1:4.8 for thiencarbazone-methyl to foramsulfuron to halosulfuron-methyl. In an aspect, the disclosure provides for a combination described herein at a ratio of about 2:1:3.1 for thiencarbazone-methyl to foramsulfuron to halosulfuron-methyl. In an aspect, the disclosure provides for a combination described herein at a ratio of about 3:2:1 for thiencarbazone-methyl to foramsulfuron to halosulfuron-methyl.

In an aspect, the combination comprising thiencarbazone-methyl, foramsulfuron, and halosulfuron-methyl is in a ratio of about 1:2:3.

In another aspect, an active compound combination described herein can be prepared, for example, by mixing an active substance with at least one surfactant, adjuvant, carrier, extender, solvent or diluent, emulsifier, dispersant and/or binder or fixing agent, wetting agent, water repellant, if appropriate siccatives and LTV stabilizers and, if appropriate, dyes and pigments, defoamers, preservatives, secondary thickeners, adhesives, gibberellins and also further processing auxiliaries.

The surfactant can be of the emulsifying or wetting type and can be ionic or non-ionic. In another aspect, the disclosure provides for surfactants that are salts of polyacrylic or lignosulfonic acids; salts of phenolsulfonic or naphthalene-sulfonic acids; polycondensates of ethylene oxide with fatty alcohols or fatty acids or fatty amines or substituted phenols (particularly alkylphenols or arylphenols); ester-salts of sulfosuccinic acids; taurine derivatives, such as alkyl taurates; phosphoric esters; or esters of alcohols or polyoxyethylated phenols.

In an aspect, the carrier refers to a natural or synthetic, organic or inorganic substance which is mixed or combined with the active substances for better applicability. The carrier, which may be solid or liquid, is generally inert and, for example, is suitable for use in agriculture.

Suitable solid or liquid carriers can be, for example, ammonium salts and ground natural minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral and vegetable oils and derivatives of these. Mixtures of such carriers may also be used. Suitable carriers for granules can be, for example, crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable liquefied gaseous extenders or carriers can be, for example, liquids which are gaseous at ambient temperature and under atmospheric pressure, for example aerosol propellants, such as halocarbons, and also butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives include mineral and vegetable oils.

If the extender used is water, it is also possible, for example, to use organic solvents as auxiliary solvents. Suitable liquid solvents can be, for example, aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water. However, sulfonylurea herbicides are often not stable long-term in water.

In another aspect, an active compound combination described herein can comprise surface-active substances. Suitable surface-active substances, for example, are emulsifiers and/or foam formers, dispersants or wetting agents having ionic or nonionic properties, or mixtures of these surface-active substances. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example, alkylaryl polyglycol ethers, alkylsulphonates, alkyl sulphates, arylsulphonates, protein hydrolysates, lignin-sulphite waste liquors and methylcellulose.

In another aspect, an active compound combination described herein can include a colorant, such as an inorganic pigment, for example phytocyanine, iron oxide, titanium oxide, Prussian blue, and an organic dye, such as alizarin dye, azo dye and metal phthalocyanine dye, and trace nutrient, such as salts of iron, manganese, boron, copper, cobalt, molybdenum and zinc.

In another aspect, an active compound combination described herein may include other additional components, for example protective colloids, binders, adhesives, thickeners, thixotropic substances, penetrants, stabilizers, sequestering agents, complex formers.

An active compound combination according to the invention are generally applied in the form of ready mixes. However, the active compounds contained in the active compound combinations may also be applied in the form of individual formulations which are mixed upon use, that is, in the form of tank mixes.

In another aspect, an active compound combination described herein can be combined with an additional actives agent, for example, an insecticide, attractant, sterilant, bactericide, acaricide, nematicide, fungicide, growth regulator, herbicide, fertilizer, safener, or biological control agent.

In an aspect, the active compound combination described herein can be combined with a pre-emergent herbicide, such as SPECTICLE® 20 WSP Herbicide (containing the active ingredient Indaziflam), SPECTICLE® FLO Herbicide (containing the active ingredient Indaziflam), RONSTAR® FLO Herbicide (containing the active ingredient Oxadiazon), or RONSTAR® WSP Herbicide (containing the active ingredient Oxadiazon), to obtain pre-emergent and post-emergent activity.

Examples of fertilizers capable of being used with the compositions and methods described herein include, for example, Urea, Ammonium Nitrate, Ammonium Sulfate, Calcium Nitrate, Diammonium Phosphate, Monoammonium phosphate, Triple Super Phosphate, Potassium Nitrate, Potassium nitrate, nitrate of potash, Potassium Chloride, muriate of potash, di and mono potassium salts of phosphite/phosphonate.

The active compound combinations can be used as such, in the form of their formulations or the use forms which can be prepared from these formulations by further dilution, such as ready-to-use solutions, suspensions, emulsions, powders, pastes and granules. Application is effected in the customary manner, for example by pouring, spraying, atomizing, dusting or broadcasting.

In an aspect, an active compound combination described herein is applied to turfgrass in a single application step. In another aspect, an active compound combination described herein is applied to a turfgrass in a multiple application steps, for example, two, three, four, five or more application steps.

In yet another aspect, an active compound combination described herein is applied to turfgrass thereof in one or more application at weed regrowth. In yet another application, an active compound combination described herein is applied to turfgrass therof in one or more application 4-6 weeks after initial application.

The instant invention is distinguishable from other herbicide treatments known in the art because in many cases only 2 applications are needed, whereas with MSMA (Monosodium methanearsonate), up to weekly applications may be needed.

In an aspect active compound combinations described herein are applied to grass in separate application steps. In another aspect, active compound combinations described herein are applied to grass as a composition in the same application step.

An active compound combination according to the invention can be applied after emergence of the plants, that is to say by the post-emergence method. Post-emergent turf herbicides are applied to existing weeds i.e., the weeds have germinated & emerged from the soil. The converse of post-emergent control is pre-emergent weed control, where the herbicide is applied to prevent germinating weed seeds from emerging from the soil.

In one aspect, an active compound combination according to the invention is applied by the post-emergence method wherein an active compound combination described herein is applied to turfgrass after the appearance of weeds in grass.

In an aspect, an active compound combination described herein can be used as in the form of suspension concentrates, aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active substance, and also microencapsulations in polymeric substances and in coating materials for seed, and also ULV cold-fogging and warm-fogging formulations.

In an aspect, an active compound combination described herein can comprise ready-to-use compositions which can be applied with suitable apparatus to the grass or the seed. In another aspect, an active compound combination described herein can be used in commercial concentrates which are diluted with water prior to use.

In an aspect, the active compound combination described herein is formulated as an about 60.5% water dispersible granule.

The disclosure also provides for applying an active compound combination described herein to turfgrass by utilizing, for example, dipping, spraying, atomizing, irrigating, evaporating, dusting, fogging, broadcasting, foaming, painting, spreading-on, drenching, or drip irrigating techniques.

In an aspect, the active compound combination described herein is applied to turfgrass by spraying. In an aspect, the active compound combination described herein is applied at a spray solution pH near 6.

In an aspect, the active compound combination described herein is sprayed on turfgrass with a spray adjuvant, for example, Nonionic Surfactant, methylated seed oil (MSO), and ammonium sulfate (AMS).

An active compound combination described herein can be applied to turfgrass. In an aspect, the active compound combination is applied as a foliar spray. In an embodiment, an active compound combination are applied with sufficient water volumes for adequate coverage of foliage, according to the weed growth stage.

In an aspect, an active compound combination described herein is applied to turfgrass, for example, warm season turfgrasses. Turf species that the described compositions can be used on include bermudagrass, and zoysiagrass of golf courses, sport fields, commercial recreational areas, and sod farms.

Examples of warm season turfgrasses can include, for example, Bermudagrass (*Cynodon* spp. L. C. Rich), zoysiagrass (*Zoysia* spp. Willd.), St. Augustine grass (*Stenotaphrum secundatum* Walt Kuntze), centipedegrass (*Eremochloa ophiuroides* Munro Hack.), carpetgrass (*Axonopus affinis* Chase), Bahia grass (*Paspalum notatum* Flugge), Kikuyugrass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.)

In an aspect, an active compound combination described herein may be applied to grass infested with weeds, such as annual and perennial grass weeds, sedges and kyllingas, and broadleaf weeds.

Such weeds include dallisgrass (*Paspalum dilatatum*), sedges (*Cyperus* spp.), kyllingas (*Kyllinga* spp.), bull *paspalum* (*Paspalum setaceum*), vaseygrass (*Paspalum urvillei*), Alexandergrass (*Brachiaria plantaginea*), tropical signalgrass (*Urochloa subquadripara*), goosegrass (*Eleusine indica*), doveweed (*Murdannia nudiflora*), creeping bentgrass (*Agrostis stolonifera*), annual bluegrass (*Poa annua*), roughstalk bluegrass (*Poa trivialis*), transition ryegrass (*lolium* spp.), tall fescue (*Schedonorus phoenix/Festuca arundinacea*), and crabgrass (*Digitaria* spp.), dollarweed/pennywort (*Hydrocotyle* spp.), spurge (*Chamaesyce* spp.), Virginia buttonweed (*Diodia virginiana*), little barley (*Hordeum pusillum*), carpetweed (*Mollugo verticillata*), common chickweed (*Stellaria media*), mouseear chickweed (*Cerastium vulgatum*), hop clover (*Trifolium* spp.), rabbitfoot clover (*Trifolium arvense*), white clover (*trifolium repens*), common vetch (*Vicia sativa*), cudweed (*Gnaphalium, Pseudognaphalium* and *Gamochaeta* spp.), cutleaf evening primrose (*Oenothera laciniata*), Carolina false dandelion (*Pyrrhopappus carolinianus*), Florida pusley (*Richardia scabra*), hairy bittercress (*Cardamine hirsuta*), henbit (*Lamium amplexicaule*), knawel (*Scleranthus annuus*), London rocket (*Sisymbrium irio*), buckhorn plantain (*Plantago lanceolata*), paleseed plantain (*Plantago virginica*), sphepherdspurse (*Capsella bursa-pastoris*), corn speedwell (*Veronica arvensis*), Texas toadflax (*Nuttallanthus texanus*), common cocklebur (*Xanthium strumarium*), Philadelphia fleabane (*Erigeron philadelphicus*), Venice mallow (*Hibiscus trionum*), maypop passionflower (*Passiflora incarnata*), redroot pigweed (*Amaranthus retroflexus*), common pokeweed (*Phytolacca Americana*), wild radish (*Raphanus raphanistrum*), common ragweed (*Ambrosia artemisiifolia*), giant ragweed (*Ambrosia trifida*), Pennsylvania smartweed (*Polygonum pensylvanicum*), common sunflower (*Helianthus annus*), velvetleaf (*Abutilon theophrasti*), bahiagrass (*Paspalum notatum*), Carolina geranium (*Geranium carolinanum*), parsley-piert (*Aphanes microcarpa*), spurge (*Chamaesyce* spp.), and yellow woodsorrel (*Oxalis stricta*).

The method of the present invention improves turfgrass by controlling weeds. Though not intending to be bound by theory, it is believed that the active compound combination described herein is readily absorbed by the foliage and translocated to the site of action in the growing points of the susceptible plant. It inhibits the enzyme acetolactase synthase (ALS), also known as acetohydroxyacid synthase (AHAS). The ALS enzyme catalyzes the first step in the biosynthesis of the essential branched chain amino acids (valine, leucine, and isoleucine). The lowered levels of ALS enzyme and branched chain amino acids trigger further biochemical events culminating in the death of the weed.

The present compositions can be applied at higher rates under severe weed growth. In an embodiment, the present compositions are used in conjunction with best turf management practices as is well known to one of ordinary skill in the art.

In an aspect, a combination described herein is applied to turfgrass at an application rate of about 0.605 to 1.936 oz active ingredient/A. In an aspect, a combination described herein is applied to turfgrass at a rate of about 0.605 oz active ingredient/A. In an aspect, a combination described herein is applied to turfgrass at a rate of about 1.21 oz active ingredient/A. In an aspect, a combination described herein is applied to turfgrass at a rate of about 1.815 oz active ingredient/A. In an aspect, a combination described herein is applied to turfgrass at a rate of about 1.936 oz active ingredient/A.

In an aspect, a combination described herein is applied to turfgrass at a seasonal maximum rate of about 3.872 oz active ingredient/A.

In an aspect, an active compound combination described herein are applied at the same time in a single application step or sequentially.

In an aspect, an active compound combination described herein are applied individually or mixed and applied at the same time.

An active compound combination of the invention can be applied by known methods. In an aspect, an active compound combination described herein is formulated as a concentrate to be diluted upon use. In another aspect, the components are separately formulated and then mixed in a tank. In yet another aspect, the concentrated formulations of the individual active substances are mixed with water in the tank and the resulting spray mixture being applied.

In an aspect, methods and compositions presented herein are directed to protecting grass under a condition of weed growth. In another aspect, methods and compositions presented herein are directed to improving grass quality, density, color.

In an aspect, methods and compositions presented herein are directed to protecting turfgrass under a condition of weed growth by controlling weeds for the present weed growing season.

In an aspect, methods and compositions presented herein are directed to protecting grass under a condition of weed growth by controlling weeds for the subsequent weed growing seasons, for example, dallisgrass.

The good herbicidal action of the new active compound combinations can be seen from the examples which follow. While the individual active compounds show weaknesses with regard to their herbicidal action, the combinations all show a very good herbicidal action which exceeds a simple sum of actions.

A synergistic effect in herbicides is present when the herbicidal action of the active compound combination exceeds the action of the active compounds when applied individually.

The expected action for a given combination of two herbicides can be calculated as follows (cf. COLBY, S. R.: "Calculating synergistic and antagonistic responses of herbicide combinations", Weeds 15, pages 20-22, 1967):
If $X$=% damage by herbicide A (active compound of the formula I) at an application rate of $p$ kg/ha and $Y$=% damage by herbicide B (active compound of the formula II) at an application rate of $q$ kg/ha and $E$=the expected damage of herbicides A+B at an application rate of $p+q$ kg/ha, then $E=X+Y-(X*Y/100)$.

Colby's formula can be extended to apply to three-way combinations. Thus if $Z$=% damage by herbicide C (active compound of the formula III) at an application rate of $r$ kg/ha and $E$=the expected damage of herbicides A+B+C at an application rate of $p+q+r$ kg/ha, then $E=X+Y+Z-(XY+XZ+YZ)/100+XYZ/10,000$ If the actual damage exceeds the calculated value, the combination has a superadditive effect, that is to say a synergistic effect.

The following examples serve to illustrate certain aspects of the disclosure and are not intended to limit the disclosure.

EXAMPLES

Example 1

Plots approximately 2-4.6 $m^2$ in size are contain a natural infestation of the weed dallisgrass. Using a $CO_2$ propelled backpack sprayer, thiencarbazone-methyl (TCM), foramsulfuron (foram), and halosulfuron-methyl (halo) are applied on their own and in a combination, by post-emergence method, to the dallisgrass, at the application rates specified. The application rates for each compound and combination are equivalent to each other. All treatments included a non-ionic surfactant. After 42 days, 48 days, and 16 weeks after treatment, the degree of damage to the plants is rated in % damage in comparison to the development of the untreated control.

The FIGURES denote:

0%=no effect (like untreated control)

100%=total destruction.

TABLE 1

| Active Ingredient | Active Ingredient Application Rate (g/ha) | Trial 1 (16 WAT) | Trial 2 (42 DAA) | Trial 3 (48 DAA) |
|---|---|---|---|---|
| foramsulfuron | 28.78 | 31.5 | 76.7 | 35 |
| thiencarbazone-methyl | 15 | 85.25 | 65 | 51 |
| halosulfuron-methyl | 69.9 | 0 | 0 | −9 |
| foram + TCM + halo (Actual) | 28.78 + 15 + 69.9 | 94.25 | 83.3 | 52 |
| foram + TCM + halo (Expected) | 28.78 + 15 + 69.9 | 89.90 | 91.85 | 65.28 |

As can be seen from Table 1, there is synergistic effect for the combination of thiencarbazone-methyl, foramsulfuron and halosulfuron-methyl in Trial 1 against dallisgrass. However, for comparison Trials 2 and 3, no such effect is seen because the trials were initiated too early prior to dallisgrass entering winter dormancy.

Example 2

Glasshouse plots approximately 1.1 $m^2$ in size are planted with the weed Tall Fescue. Using a 1 nozzle motorized track sprayer, thiencarbazone-methyl (BYH18636), foramsulfuron (Revolver●), and halosulfuron-methyl (Sedgehammer●) are applied on their own and in combination with each other (a combination of thiencarbazone-methyl, foramsulfuron, and halosulfuron-methyl is SP 102000025052), by post-emergence method, to the weed Tall Fescue, at the application rates specified. The application rates for each compound and combination are equivalent to each other.

After 14 and 27 days after treatment, the degree of damage to the plants is rated in % damage in comparison to the development of the untreated control.

The FIGURES denote:

0%=no effect (like untreated control)

100%=total destruction.

TABLE 2

| Entry No. | Entry Type | Entry/Trt. Description | Dosage | Dosage Unit | Transformed Dosage | Transformed Dosage Unit | 0 DAA | 14 DAA | 27 DAA |
|---|---|---|---|---|---|---|---|---|---|
| 1 | PRODUCT | UNTREATED UNTREATED | | | | | 0 | 0 | 0 |
| 3 | PRODUCT | BYH18636 THIENCARBAZONE-METHYL | 14.58 14.58 | G A/HA | 0.2973 | OZ/A | 0 | 26.3 | 52.5 |
| | PROD_ADJ | NIS NON-IONIC SURFACTANT | 0.25 750 | % V/V g Al | 0.25 | % V/V | | | |
| 4 | PRODUCT | REVOLVER (NEW FORMULATION) FORAMSULFURON | 29.12 29.12 | G A/HA | 17.63 | OZ/A | 0 | 7.5 | 27.5 |
| | PROD_ADJ | NIS NON-IONIC SURFACTANT | 0.25 750 | % V/V g Al | 0.25 | % V/V | | | |
| 5 | PRODUCT | SEDGEHAMMER TURF HERB HALOSULFURON-METHYL | 45.3 45.3 | G A/HA | 0.862 | OZ/A | 0 | 0 | 0 |
| | PROD_ADJ | NIS NON-IONIC SURFACTANT | 0.25 750 | % V/V g Al | 0.25 | % V/V | | | |
| 6 | PRODUCT | BYH18636 THIENCARBAZONE-METHYL | 14.58 14.58 | G A/HA | 0.2973 | OZ/A | 0 | 51.3 | 76.3 |
| | PRODUCT | REVOLVER (NEW FORMULATION) FORAMSULFURON | 29.12 29.12 | G A/HA | 17.63 | OZ/A | | | |
| | PROD_ADJ | NIS NON-IONIC SURFACTANT | 0.25 750 | % V/V g Al | 0.25 | % V/V | | | |
| 7 | PRODUCT | BYH18636 THIENCARBAZONE-METHYL | 14.58 14.58 | G A/HA | 0.2973 | OZ/A | 0 | 33.8 | 62.5 |
| | PRODUCT | SEDGEHAMMER TURF HERB HALOSULFURON-METHYL | 45.3 45.3 | G A/HA | 0.862 | OZ/A | | | |
| | PROD_ADJ | NIS NON-IONIC SURFACTANT | 0.25 750 | % V/V g Al | 0.25 | % V/V | | | |
| 8 | PRODUCT | REVOLVER (NEW FORMULATION) FORAMSULFURON | 29.12 29.12 | G A/HA | 17.63 | OZ/A | 0 | 12.5 | 26.3 |
| | PRODUCT | SEDGEHAMMER TURF HERB HALOSULFURON-METHYL | 45.3 45.3 | G A/HA | 0.862 | OZ/A | | | |
| | PROD_ADJ | NIS NON-IONIC SURFACTANT | 0.25 750 | % V/V g Al | 0.25 | % V/V | | | |
| 2 | PRODUCT | SP102000025052 (ACTUAL) THIENCARBAZONE-METHYL FORAMSULFURON HALOSULFURON-METHYL | 89 14.58 29.12 45.3 | G A/HA | 2.1 | OZ/A | 0 | 55 | 82.5 |
| | PROD_ADJ | NIS NON-IONIC SURFACTANT | 0.25 750 | % V/V g Al | 0.25 | % V/V | | | |
| — | | TCM + foram + halo + NIS (EXPECTED) | | | | | | 31.83 | 65.56 |
| 10 | PRODUCT | BYH18636 THIENCARBAZONE-METHYL | 22.2 22.2 | G A/HA | 0.4527 | OZ/A | 0 | 42.5 | 75 |
| | PROD_ADJ | NIS NON-IONIC SURFACTANT | 0.25 750 | % V/V g Al | 0.25 | % V/V | | | |
| 11 | PRODUCT | REVOLVER (NEW FORMULATION) FORAMSULFURON | 44.37 44.37 | G A/HA | 26.87 | OZ/A | 0 | 12 | 26.3 |
| | PROD_ADJ | NIS NON-IONIC SURFACTANT | 0.25 750 | % V/V g Al | 0.25 | % V/V | | | |
| 12 | PRODUCT | SEDGEHAMMER TURF HERB HALOSULFURON-METHYL | 69 69 | G A/HA | 1.313 | OZ/A | 0 | 0 | 0 |
| | PROD_ADJ | NIS NON-IONIC SURFACTANT | 0.25 750 | % V/V g Al | 0.25 | % V/V | | | |
| 13 | PRODUCT | BYH18636 THIENCARBAZONE-METHYL | 22.2 22.2 | G A/HA | 0.4527 | OZ/A | 0 | 35 | 75 |
| | PRODUCT | REVOLVER (NEW FORMULATION) FORAMSULFURON | 44.37 44.37 | G A/HA | 26.87 | OZ/A | | | |
| | PROD_ADJ | NIS NON-IONIC SURFACTANT | 0.25 750 | % V/V g Al | 0.25 | % V/V | | | |
| 14 | PRODUCT | BYH18636 THIENCARBAZONE-METHYL | 22.2 22.2 | G A/HA | 0.4527 | OZ/A | 0 | 22.5 | 63.8 |
| | PRODUCT | SEDGEHAMMER TURF HERB HALOSULFURON-METHYL | 69 69 | G A/HA | 1.313 | OZ/A | | | |
| | PROD_ADJ | NIS NON-IONIC SURFACTANT | 0.25 750 | % V/V g Al | 0.25 | % V/V | | | |
| 15 | PRODUCT | REVOLVER (NEW FORMULATION) FORAMSULFURON | 44.37 44.37 | G A/HA | 26.87 | OZ/A | 0 | 12.5 | 28.8 |
| | PRODUCT | SEDGEHAMMER TURF HERB HALOSULFURON-METHYL | 69 69 | G A/HA | 1.313 | OZ/A | | | |
| | PROD_ADJ | NIS NON-IONIC SURFACTANT NON-IONIC SURFACTANT | 0.25 750 | % V/V g Al | 0.25 | % V/V | | | |
| 9 | PRODUCT | SP102000025052 THIENCARBAZONE-METHYL FORAMSULFURON HALOSULFURON-METHYL | 135.6 22.2 44.37 69 | G A/HA | 3.2 | OZ/A | 0 | 43.6 | 66.3 |

TABLE 2-continued

| Entry No. | Entry Type | Entry/Trt. Description | Dosage | Dosage Unit | Transformed Dosage | Transformed Dosage Unit | 0 DAA | 14 DAA | 27 DAA |
|---|---|---|---|---|---|---|---|---|---|
| | PROD_ADJ | NIS NON-IONIC SURFACTANT | 0.25 750 | % V/V g AI | 0.25 | % V/V | | | |
| — | | TCM + foram + halo + NIS (EXPECTED) | | | | | | 49.4 | 81.58 |

According to Colby, the formulas are most accurate when values of X, Y, and Z are near the 50% level since the dose-response curves deviate least from linearity at the 50% level. A dose response was conducted on the 3-way blend against tall fescue in the greenhouse. Through this experiment, it was determined the 'correct' dose for testing in the greenhouse was 2.1 oz./A (1.271 oz active ingredient/A). As can be seen from Table 2, there is synergistic effect for the combination of thiencarbazone-methyl, foramsulfuron and halosulfuron-methyl at an application rate of 2.1 oz/A (1.271 oz active ingredient/A) against the weed tall fescue. However, no such effect is seen at a higher application rate of 3.2 oz/A (1.936 oz active ingredient/A).

The invention claimed is:

1. A method of controlling weeds in turf grass comprising applying an effective amount of a combination comprising thiencarbazone-methyl and at least one sulfonylurea herbicide, to the weeds at a time which is post-emergence of said weeds, wherein the combination comprising thiencarbazone-methyl and the at least one sulfonylurea herbicide is applied to said weeds at a rate of about 0.605 to 1.936 oz of the total of the thiencarbazone-methyl and the at least one sulfonylurea herbicide/A.

2. The method according to claim 1, wherein thiencarbazone-methyl is present at about 5% to 15% by weight based on the total weight of the combination.

3. The method according to claim 1, wherein the at least one sulfonylurea herbicide is selected from the group consisting of foramsulfuron and halosulfuron-methyl.

4. The method according to claim 1, wherein the combination acts synergistically.

5. The method according to claim 1, wherein thiencarbazone-methyl and at least one sulfonylurea herbicide are the only active compounds in the combination.

6. The method according to claim 1, wherein the thiencarbazone-methyl and the at least one sulfonylurea herbicide are applied at a ratio of about 0.5 to 50:0.5 to 15 of (i) thiencarbazone-methyl to (ii) sulfonylurea herbicide.

7. The method according to claim 1, wherein the at least one sulfonylurea herbicide is selected from the group consisting of foramsulfuron, flazasulfuron, rimsulfuron, halosulfuron-methyl, sulfosulfuron, and trifloxysulfuron-sodium.

8. The method according to claim 1, wherein the weeds are selected from the group consisting of dallisgrass, sedges, kyllingas, bull *paspalum*, vaseygrass, Alexandergrass, tropical signalgrass, tall fescue, crabgrass, dovewced, goosegrass, transition ryegrass, Virginia buttonweed, creeping bentgrass, little barley, carpetweed, common chickweed, mouseear chickweed, hop clover, rabbitfoot clover, white clover, common vetch, cudweed, cutleaf evening primrose, Carolina false dandelion, Florida pusley, hairy bittercress, henbit, knawel, London rocket, buckhorn plantain, paleseed plantain, shepherspurse, corn speedwell, Texas toadflax, annual bluegrass, roughstalk bluegrass, bahiagrass, Carolina *geranium*, common cocklebur, dollarweed/pennywort, Philadelphia fleabane, Venice mallow, parsley-piert, maypop passionflower, redroot pigweed, common pokeweed, wild radish, common ragweed, giant ragweed, Pennsylvania smartweed, spurge, sunflower, velvetleaf, and yellow woodsorrel.

9. The method according to claim 1, wherein the weeds are selected from the group consisting of crabgrass, dallisgrass, dovewced, goosegrass, sedges, kyllingas, transition ryegrass, tropical signalgrass, and Virginia buttonweed.

10. The method according to claim 1, wherein the turfgrass is warm season turfgrass.

11. The method according to claim 10, wherein the turfgrass is bermudagrass or zoysiagrass.

12. The method according to claim 1, wherein the weeds are controlled for at least one subsequent turf growing season.

13. The method according to claim 1, wherein the thiencarbazone-methyl and the at least one sulfonylurea herbicide are in water-dispersible granule form.

14. The method according to claim 1, wherein the thiencarbazone-methyl and the at least one sulfonylurea herbicide are applied together or sequentially.

15. The method according to claim 1, wherein the thiencarbazone-methyl and the at least one sulfonylurea herbicide are applied to the weeds by spraying.

16. The method according to claim 1, wherein thiencarbazone-methyl and sulfonylurea herbicide are present at a ratio of about 0.5 to 25:0.5-10.

* * * * *